(12) United States Patent
Simig et al.

(10) Patent No.: US 7,326,794 B2
(45) Date of Patent: Feb. 5, 2008

(54) PROCESS FOR THE PREPARATION OF HIGH PURITY PERINDOPRIL AND INTERMEDIATES USEFUL IN THE SYNTHESIS

(75) Inventors: Guyla Simig, Budapest (HU); Tibor Mezei, Budapest (HU); Marta Porcs-Makkay, Pomaz (HU); Attila Mandi, Budapest (HU)

(73) Assignee: Les Laboratoires Servier, Courbevoie Cedex (FR)

( * ) Notice: Subject to any disclaimer, the term of this patent is extended or adjusted under 35 U.S.C. 154(b) by 456 days.

(21) Appl. No.: 10/503,272

(22) PCT Filed: Jan. 29, 2003

(86) PCT No.: PCT/IB03/00691

§ 371 (c)(1),
(2), (4) Date: Jul. 29, 2004

(87) PCT Pub. No.: WO03/064388

PCT Pub. Date: Aug. 7, 2003

(65) Prior Publication Data

US 2005/0119492 A1    Jun. 2, 2005

(30) Foreign Application Priority Data

Jan. 30, 2002    (EP)    ..................    02290206

(51) Int. Cl.
C07D 209/42    (2006.01)
(52) U.S. Cl. .................................................. 548/492
(58) Field of Classification Search ................. 548/492
See application file for complete search history.

(56) References Cited

U.S. PATENT DOCUMENTS 4,914,214 A * 4/1990 Vincent et al. ............ 548/492

6,835,843 B2    12/2004 Langlois et al.
7,060,842 B2    6/2006 Mezei et al.
2004/0248814 A1    12/2004 Cid

FOREIGN PATENT DOCUMENTS

| DE | 19721290 | 11/1997 |
|---|---|---|
| EP | 0308341 | 3/1989 |
| EP | 1256590 | 11/2002 |
| EP | 1279665 | 1/2003 |
| GB | 2095252 | 9/1982 |
| WO | WO 01/58868 | 8/2001 |

OTHER PUBLICATIONS

Vincent, et al., Drug Design and Discovery, 1992, 9, Nov. 28.
Vincent, M., et al., "Synthesis and Ace Inhibitory Activity of the Stereoisomers of Perindopril (S9490) and Perindoprilate (S 9780)" Drug Design and Discovery, Hardwood Academic Publishers GmbH, vol. 9, No. 1, 1992, pp. 11-28 XP000885876 ISSN: 1055-9612, p. 11-p. 13.

* cited by examiner

Primary Examiner—Joseph K. McKane
Assistant Examiner—Susannah L. Chung
(74) Attorney, Agent, or Firm—Hueschen and Sage

(57) ABSTRACT

The invention relates to 1-{2(S)-[1(S)-(ethoxycarbonyl)butylamino]propionyl}-(3aS,7aS)octahydroindol-2(S)-carboxylic acid of the Formula I and the t-butylamine salt of the Formula I' thereof free of contaminations derivable from dicyclohexyl carbodiimide, and a process for the preparation thereof.

The invention also relates to new intermediates of the general Formula III (wherein R stands for lower alkyl or aryl lower alkyl).

The compound of the Formula I—perindopril—is a known ACE inhibitor.

16 Claims, No Drawings

PROCESS FOR THE PREPARATION OF HIGH PURITY PERINDOPRIL AND INTERMEDIATES USEFUL IN THE SYNTHESIS

This invention relates to a process for the preparation of high purity perindopril and intermediates useful in the synthesis of perindopril.

More particularly the invention is concerned with a process for the synthesis of high purity perindopril free of certain contaminations, intermediates useful in the synthesis and a process for the preparation of said intermediates.

Perindopril—particularly the t-butylamine salt thereof—possesses useful pharmacological properties. The main activity of perindopril is the inhibition of the conversion of the enzyme Angiotensine I (or kininase II) into the octapeptide Angiotensine II; thus it is an ACE inhibitor. The above beneficial effect of perindopril enables the use of this active ingredient in the treatment of cardiovascular diseases, particularly arterial hypertension and cardial insufficiency.

Perindopril is mentioned the first time in EP 0,049,658. However the synthesis of perindopril is not exemplified.

An industrial scale perindopril synthesis is described in EP 0,308,341. The structures of the compounds of formula I to XII, I', VII' and VIII' are described in the annex. According to this process the compound of the Formula V is reacted with the compound of the Formula II in the presence of dicyclohexyl carbodiimide and 1-hydroxy-benzotriazole, whereafter the benzyl ester of the Formula VI is debenzylated to give perindopril of the Formula I, which is then converted into the salt of the Formula I' by reacting with t-butylamine.

The drawback of this process is that the purity of the perindopril thus obtained is not satisfactory and for this reason a series of purification steps is required to provide a product which meets the severe quality requirements of pharmaceutical active ingredients. The reason of said disadvantage is that the coupling reaction of the compounds of the Formulae V and II is carried out in the presence of dicyclohexyl carbodiimide which results in the formation of a considerable amount of contaminations of the benzyl esters of the Formulae VII and VIII which are transformed by debenzylation into the compounds of the Formulae VII' and VIII'. The removal of said contaminations is encountered with significant difficulties.

According to unpublished French patent application 01.09839 dihydroindole-2-carboxylic acid or its ester of the general Formula IX (wherein $R^1$ stands for hydrogen or lower alkyl containing 1-6 carbon atoms) is reacted with a compound of the general Formula X (wherein $R^2$ is an amino protecting group) in an organic solvent, in the absence or in the presence of not more than 0.6 mole of 1-hydroxy-benzotriazole, related to 1 mole of the compound of the general Formula IX, and 1-1.2 mole of dicyclohexyl carbodiimide, related to 1 mole of the compound of the Formula IX, subjecting the compound of the general Formula XI thus obtained (wherein $R^1$ and $R^2$ are as stated above) to catalytic hydrogenation and converting the compound of the Formula XII thus obtained (wherein $R^1$ and $R^2$ are as stated above) into perindopril in a known manner.

It is the object of the present invention to provide a process for the preparation of high purity perindopril free of contaminations derivable from dicyclohexyl carbodiimide, particularly compounds of the Formulae VII' and VIII'.

The above object is solved with the aid of the process and new intermediates of the present invention.

According to an aspect of the present invention there is provided 1-{2(S)-[1(S)-(ethoxycarbonyl)butylamino]propionyl}-(3aS,7aS)octahydroindol-2(S)-carboxylic acid of the Formula I and the t-butylamine salt of the Formula I' thereof free of contaminations derivable from dicyclohexyl carbodiimide.

According to a particular embodiment of the above aspect of the present invention there is provided 1-{2(S)-[1(S)-(ethoxycarbonyl)butylamino]propionyl}-(3aS,7aS)octahydroindol-2(S)-carboxylic acid of the Formula I and the t-butylamine salt of the Formula I' thereof free of compounds of the Formula VII' and VIII'.

According to a further aspect of the present invention there is provided a process for the preparation of the compound of the Formula I and the t-butylamine salt of the Formula I' thereof free of contaminations derivable from dicyclohexyl carbodiimide, particularly free of compounds of the Formula VII' and VIII' which comprises reacting the compound of the Formula II with a suitable carbonic acid derivative; activating the compound of the general Formula III thus obtained (wherein R stands for lower alkyl or aryl-lower alkyl) with thionyl chloride; reacting the activated compound thus obtained with a compound of the Formula IV and if desired reacting the compound of the Formula I thus obtained with t-butylamine.

According to a still further aspect of the present invention there are provided compounds of the general Formula III (wherein R stands for lower alkyl or aryl-lower alkyl).

According to a still further aspect of the present invention there is provided a process for the preparation of compounds of the general Formula III (wherein R stands for lower alkyl or aryl-lower alkyl) which comprises reacting the compound of the Formula II with a suitable carbonic acid derivative.

According to a still further aspect of the present invention there are provided pharmaceutical compositions comprising 1-{2(S)-[1(S)-(ethoxycarbonyl)butylamino]propionyl}-(3aS,7aS)octahydroindol-2(S)-carboxylic acid of the Formula I and the t-butylamine salt of the Formula I' thereof free of contaminations derivable from dicyclohexyl carbodiimide as active ingredient in admixture with suitable inert pharmaceutical carriers.

According to a still further aspect of the present invention there is provided the use of 1-{2(S)-[1(S)-(ethoxycarbonyl)butylamino]propionyl}-(3aS,7aS)octahydroindol-2(S)-carboxylic acid of the Formula I and the t-butylamine salt of the Formula I' thereof free of contaminations derivable from dicyclohexyl carbodiimide as pharmaceutical active ingredient, particularly as ACE inhibitor.

According to a still further aspect of the present invention there is provided a method of antihypertensive treatment which comprises administering to the patient in need of such treatment a pharmaceutically active amount of 1-{2(S)-[1(S)-(ethoxycarbonyl)butylamino]propionyl}-(3aS,7aS)octahydroindol-2(S)-carboxylic acid of the Formula I and the t-butylamine salt of the Formula I' thereof free of contaminations derivable from dicyclohexyl carbodiimide.

Synthesis of a peptide bond normally involves the reaction of a carboxy activated N-protected amino-acid with a carboxy protected amino acid. N-Acyl-, or more specifically N-alkoxycarbonyl amino-acid chlorides (derived from acids of Formula III) represent one of the classical groups of carboxy activated N-protected amino-acid derivatives.

Two methods are known to form a peptide bond starting from N-alkoxycarbonyl amino-acid chlorides (see: Houben-Weyl: Methoden der Organischen Chemie Band XV/II, pp. 355-363):

reaction with amino-acid esters in organic solvent in the presence of equivalent base, reaction with amino acids in alkaline aqueous solution (under Schotten-Baumann conditions).

In the modern practise, amino-acid chlorides are considered as over-reactive species leading to undesired side reactions, therefore alternative carboxy activation methods, e.g. the use of DCC, are preferred (see: R. C. Sheppard: Peptide Synthesis in Comprehensive Organic Chemistry, Vol. 5, pp. 339-352, edited by E. Haslam, Pergamon Press, Oxford, 1994).

The present invention is based on the recognition that the new N-alkoxy(aralkoxy)carbonyl amino-acids of general Formula III can be successfully activated with thionyl chloride and the activated carboxylic acid derivative thus obtained can be preferably used for the acylation of the amino-acid of Formula IV in an organic solvent to form the required compound of Formula I in a single reaction step. This recognition is surprising in several respect: the reaction is carried out in organic solvent in the absence of base and not in alkaline water as suggested by prior art; the "over-reactive" character of the amino acid-chlorides mentioned above does not cause inconvenient side reactions, and the alkoxy(aralkoxy)carbonyl protecting group is removed during the peptide formation process. This recognition is so much the more surprising as in all the actually disclosed syntheses of perindopril the carbonic acid derivative was always activated with dicyclohexyl carbodiimide causing the formation of undesired contaminations. The use of thionyl chloride as activating agent is highly advantageous. On the one hand no difficultly removable by-products are formed, while on the other gaseous hydrogen chloride and sulphur dioxide formed in the reaction can be easily eliminated from the reaction mixture.

The definitions used in the patent specification and the claims are to be interpreted as follows.

The term "lower alkyl" relates to straight or branched chain alkyl groups containing 1-6 carbon atoms (e.g. methyl, ethyl, n-propyl, isopropyl, n-butyl, secondary butyl, tertiary-butyl, n-pentyl, n-hexyl etc.), preferably methyl, ethyl or tertiary butyl.

The term "aralkyl" relates to alkyl groups as defined above substituted by one or two aryl groups (e.g. benzyl, beta-phenyl-ethyl, beta-beta-diphenyl-ethyl etc.; preferably benzyl).

According to the first step of the perindopril synthesis according to the present invention the compound of the Formula II is acylated with a suitable carbonic acid derivative. The process is carried out in a manner known per se. As carbonic acid derivative preferably the corresponding alkyl chloroformates or di-alkyl-dicarbonates can be used. The methoxycarbonyl, ethoxycarbonyl and benzyloxycarbonyl group may be preferably introduced with the aid of methyl chloroformate, ethyl chloroformate and benzyl chloroformate, respectively. The tertiary butoxycarbonyl group may be introduced preferably by using di-tertiary butyl dicarbonate. The acylation reaction is carried out in an inert organic solvent and in the presence of a base. As inert organic solvent preferably halogenated aliphatic hydrocarbons (e.g. dichloromethane, dichloroethane or chloroform), esters (e.g. ethyl acetate) or ketones (e.g. acetone), can be used. One may preferably use acetone as solvent. The reaction may be carried out in the presence of an inorganic or organic base. As inorganic base preferably alkali carbonates (e.g. sodium carbonate or potassium carbonate) or alkali hydrogen carbonates (e.g. sodium hydrogen carbonate or potassium hydrogen carbonate) can be used. As organic base preferably trialkyl amines (e.g. triethylamine) or pyridine can be used. One may preferably use an alkali carbonate or triethylamine as base.

The reaction is preferably carried out at temperature between 0° C. and 30° C., particularly at ambient temperature. One may proceed preferably by preparing the reaction mixture at a low temperature of about 0-5° C., then allowing the reaction mixture to warm to ambient temperature and carrying out the reaction at this temperature for a period of some hours.

The reaction mixture is worked up in the usual manner. One may proceed preferably by treating the reaction mixture after evaporation with an acid, extracting the mixture with an organic solvent, extracting the organic phase with an aqueous alkali hydroxide solution, acidifying the aqueous layer and extracting the compound of the general Formula III obtained into an organic solvent. The crude product obtained on evaporating the organic phase can be directly used for the further reaction without any purification.

The compounds of the general Formula III thus obtained are new and are also subject matter of the present invention.

According to the next step of the perindopril synthesis of the present invention the compound of the general Formula III is activated with thionyl chloride. In this step thionyl chloride is used in an excess, preferably in a molar ratio of 1.1-2—particularly 1.5-1.7—related to 1 mole of the compound of the general Formula III. The reaction is carried out in an inert organic solvent. As reaction medium preferably halogenated aliphatic hydrocarbons (e.g. dichloromethane, dichloroethane or chloroform), esters (e.g. ethyl acetate) or ethers (e.g. diethyl ether, tetrahydrofurane, dioxane) can be used. One may carry out the reaction particularly advantageously in dichloro-methane as medium. The reaction is carried out at the temperature between 0° C. and 30° C., particularly at ambient temperature. One may proceed preferably by preparing the reaction mixture at a lower temperature of 0-5° C., thereafter allowing the reaction mixture to warm to ambient temperature and carrying out the reaction at this temperature for a few hours. The activation with thionyl chloride being completed the excess of thionyl chloride is removed together with the hydrochloric acid and sulphur dioxide.

The activated compound obtained from the compound of the general Formula III is reacted with a compound of the Formula IV. The compound of the Formula IV is perhydroindole-2-carboxylic acid. The reaction is carried out in an inert organic solvent. As a reaction medium preferably a halogenated aliphatic hydrocarbon (e.g. dichloromethane, dichloroethane or chloroform), ester (e.g. ethyl acetate) or ether (e.g. ethyl ether, tetrahydrofurane or dioxane) can be used. One may carry out the reaction preferably in tetrahydrofurane or dichloromethane as medium. The reaction is carried out under heating, preferably at the boiling point of the reaction mixture, advantageously under reflux. The reaction takes place within a few hours. The compound of the Formula IV is used in an amount of 0.5-0.9, preferably 0.7-0.8 moles, related to 1 mole of compound of the general Formula III. The acylation reaction being completed the reaction mixture is concentrated in vacuo.

Perindopril of the Formula I may be converted into the t-butylamine salt of the Formula I' by reaction with t-butylamine. Salt formation may be carried out in a manner known per se. The salt formation reaction is carried out in an inert organic solvent, preferably ethyl acetate. t-Butylamine is used preferably in approximately equimolar amount.

1-{2(S)-[1(S)-(ethoxycarbonyl)butylamino]propionyl}-(3aS,7aS)octahydroindol-2(S)-carboxylic acid of the Formula I and the t-butylamine salt of the Formula I' thereof free of contaminations derivable from dicyclohexyl carbodiimide can be used in therapy in the form of pharmaceutical compositions. The preparation of said pharmaceutical compositions, the dosage forms and the daily dosage scheme are similar to those described in prior art for the formulation and pharmaceutical use of perindopril.

The starting material of the Formula II is described in EP 0,308,340, EP 0,308,341 and EP 0,309,324. The acid of the Formula IV is described in EP 0,308,339 and EP 0,308,341.

The advantage of the present invention is that it provides highly pure perindopril free of contaminations derivable from dicyclohexyl carbodiimide. The process is simple and can be easily scaled up. The particular advantage of the present invention is that the use of dicyclohexyl carbodiimide is completely eliminated and therefore there is not even a theoretical possibility of the formation of contaminations which may be derived from dicyclohexyl carbodiimide. Further advantage: the acylation can be carried out with the acid of the Formula IV. Protection of the carboxylic group is not required.

Further details of the present invention are to be found in the following Examples without limiting the scope of protection to said Examples.

EXAMPLES

Preparation of N-[2-(ethoxycarbonyl)butyl]-N-alkoxycarbonylalanine

Example 1

N-[2-(ethoxycarbonyl)butyl]-N-ethoxycarbonylalanine

To a suspension of N-[2-(ethoxycarbonyl)butyl]alanine (21.7 g, 100 mmol) in acetone (250 mL) was added a solution of triethylamine (27.7 mL, 20.2 g, 200 mmol) in acetone (50 mL) followed by ethyl chloroformate (24.8 mL, 28.2 g, 260 mmol) at 0-5° C. After stirring for 2 h at ambient temperature the solvent was evaporated and the residue was stirred with a mixture of water (200 mL) and concentrated hydrochloric acid (2 mL) for 8 h at ambient temperature. The mixture was extracted with ethyl acetate (200 mL) and the solution in ethyl acetate was extracted with cold aqueous sodium hydroxide solution [prepared from ice (100 g) and aqueous sodium hydroxide solution (1N, 200 mL)]. Concentrated hydrochloric acid (15 mL) was added to the aqueous layer and the mixture was extracted with ethyl acetate (200 mL). After drying and evaporation N-[2-(ethoxycarbonyl)butyl]-N-ethoxycarbonylalanine (23.8 g, 82%) was obtained as a yellow oil which can be used in the next reaction without further purification.

IR (film): 3500-2400 (OH st), 1709 (C═O st), ~1200 (C—O st), 898 (OH out of plane b), cm$^{-1}$.

$^1$H-NMR (CDCl$_3$, TMS, 400 MHz): $\delta$10.14 (1H, bs, COOH), 4.99 and 4.58 (1H, dd, J=4.5, 10.0 Hz, N—CH—CH$_2$—CH$_2$—CH$_3$), 4.29 (2H, q, J=7.1 Hz, N—C(O)—O—CH$_2$—CH$_3$), 4.24-4.13 (2H, m, CH—C(O)—O—CH$_2$—CH$_3$), 3.84 (1H, q, J=6.9 Hz, CH$_3$—CH), [2.08-1.97 (1H, m) and 1.74-1.62 (1H, m) N—CH—CH$_2$—CH$_2$—CH$_3$], 1.56-1.42 (2H, m, N—CH—CH$_2$—CH$_2$—CH$_3$), 1.51 (3H, d, J=6.9 Hz, CH$_3$—CH), 1.33 (3H, t, J=7.2 Hz, CH—C(O)—O—CH$_2$—CH$_3$), 1.27 (3H, t, J=7.1 Hz, N—C(O)—O—CH$_2$—CH$_3$), 0.99 (3H, t, J=7.3 Hz, N—CH—CH$_2$—CH$_2$—CH$_3$).

$^{13}$C-NMR (CDCl$_3$, TMS, 400 MHz): $\delta$176.4 and 175.8, 172.5, 155.8, 63.0, 62.7, 58.9, 53.8, 31.4, 19.8, 16.6, 14.0, 13.9, 13.5. (signals of the main rotamer)

Example 2

N-[2-(ethoxycarbonyl)butyl]-N-methoxycarbonylalanine

To a suspension of N-[2-(ethoxycarbonyl)butyl]alanine (4.35 g, 20 mmol) in acetone (50 mL) was added a solution of triethylamine (5.5 mL, 4.05 g, 40 mmol) in acetone (10 mL) followed by methyl chloroformate (4.0 mL, 4.91 g, 52 mmol) at 0-5° C. After stirring for 2 h at ambient temperature the solvent was evaporated and the residue was stirred with a mixture of water (40 mL) and concentrated hydrochloric acid (0.4 mL) for 8 h at ambient temperature. The mixture was extracted with ethyl acetate (40 mL) and the solution in ethyl acetate was extracted with cold aqueous sodium hydroxide solution [prepared from ice (20 g) and aqueous sodium hydroxide solution (1N, 40 mL)]. Concentrated hydrochloric acid (3 mL) was added to the aqueous layer and the mixture was extracted with ethyl acetate (40 mL). After drying and evaporation N-[2-(ethoxycarbonyl)butyl]-N-methoxycarbonylalanine (3.84 g, 70%) was obtained as a yellow oil which can be used in the next reaction without further purification.

IR (film): ~3400 (OH st), 1713 (C═O st ), 1294 (OH in plane b), 1205 (C—O st ester) cm$^{-1}$.

$^1$H-NMR (CDCl$_3$, TMS, 400 MHz): $\delta$~10.2 (1H, bs, COOH), 5.00 and 4.60 (1H, s, CH—CH$_2$—CH$_2$—CH$_3$), 4.28 (2H, q, J=7.2 Hz, O—CH$_2$—CH$_3$), 3.96 and 3.85 (1H, m, CH—CH$_3$), 3.75 (3H, s, OCH$_3$), [2.10-1.98 (1H, m) and 1.74-1.62 (1H, m) CH—CH$_2$—CH$_2$—CH$_3$], 1.56-1.42 (2H, m, CH—CH$_2$—CH$_2$—CH$_3$), 1.50 (3H, d, J=6.9 Hz, CH—CH$_3$), 1.33 (3H, t, J=7.2 Hz, 3).

Example 3

N-[2-(ethoxycarbonyl)butyl]-N-t-butyloxycarbonylalanine

To a suspension of N-[2-(ethoxycarbonyl)butyl]alanine (1.1 g, 5 mmol) and potassium carbonate (0.76 g, 5.5 mmol) in acetone (15 mL) was added di-t-butyl dicarbonate (1.20 g, 5.5 mmol) and water (1.25 mL) at 0-5° C. After stirring for 2 h at ambient temperature the mixture was cooled and the solid precipitation was filtered off. Ethyl acetate (15 mL), ice (5 g) and aqueous NaOH solution (1N, 10 mL) was added. After stirring for 5 min the layers were separated. Concentrated hydrochloric acid (1.5 mL) was added to the aqueous layer and the mixture was extracted with ethyl acetate (15 mL). After drying and evaporation N-[2-(ethoxycarbonyl)butyl]-N-t-butyloxycarbonylalanine (0.61 g, 38%) was obtained as a yellow oil which can be used in the next reaction without further purification.

IR (KBr): ~3400 (OH st), 1705 (C═O st acid), 1299 (OH in plane b)~1690 (C═O st amide), 1771 (C═O st ester), 1159 (C—O st ester) cm$^{-1}$.

$^1$H-NMR (CDCl$_3$, TMS, 400 MHz): $\delta$~9.2 (1H, bs, COOH), 5.00 (1H, dd, J=4.4, 10.2 Hz, CH—CH$_2$—CH$_2$—CH$_3$), 4.29 (2H, q, J=7.1 Hz, O—CH$_2$—CH$_3$), 3.69 (1H, q, J=6.8 Hz, CH—CH$_3$), [2.10-1.98 (1H, m) and 1.70-1.56 (1H, m), CH—CH$_2$—CH$_2$—CH$_3$], 1.56-1.42 (2H, m, CH—CH$_2$—CH$_2$—CH$_3$), 1.49 (3H, d, J=6.8 Hz, CH—C$\underline{H}$$_3$), 1.46 (9H, s, C(CH$_3$)$_3$), 1.34 (3H, t, J=7.1 Hz, O—CH$_2$—C$\underline{H}$$_3$), 0.99 (3H, t, J=7.3 Hz, CH—CH$_2$—CH$_2$—C$\underline{H}$$_3$).

Example 4

N-[2-(ethoxycarbonyl)butyl]-N-benzyloxycarbonyla-lanine

To a suspension of N-[2-(ethoxycarbonyl)butyl]alanine (2.2 g, 10 mmol) and potassium carbonate (2.2 g, 16 mmol) in a mixture of acetone (30 mL) and water (2.5 mL) was added benzyl chloroformate (2.0 mL, 2.4 g, 14 mmol) at 0-5° C. After stirring for 2 h at ambient temperature the solid was filtered off, the solvent was evaporated, the residue was stirred with cold aqueous sodium hydroxide solution [prepared from ice (20 g) and aqueous sodium hydroxide solution (1N, 40 mL)] and extracted with ethyl acetate (40 mL). The aqueous layer was acidified with an aqueous solution of hydrochloric acid 1/1 (20 mL) and the mixture was extracted with ethyl acetate (40 mL). After drying and evaporation N-[2-(ethoxycarbonyl)butyl]-N-benzyloxycar-bonylalanine (1.66 g, 47%) was obtained as a yellow oil which can be used in the next reaction without further purification.

IR (film): ~3400 (OH st), 1710 (C=O st), 699 (CH arom)cm$^{-1}$.

$^1$H-NMR (CDCl$_3$, TMS, 400 MHz): δ~9.0 (1H, bs, COOH), 5.00 (5H, m, Ph), 5.2-5.1 (2H, m, Ph-C$\underline{H}$$_2$), 4.96 and 4.57 (1H, dd, J=9.6, 4.8, N—C$\underline{H}$—CH$_2$—CH$_2$—CH$_3$), 4.26 and 4.12 (2H, q, J=7.1 Hz, O—C$\underline{H}$$_2$—CH$_3$), 4.02 and 3.89 (1H, q, J=6.9 Hz, C$\underline{H}$—CH$_3$), [2.10-1.93 (1H, m) and 1.72-1.62 (1H, m), CH—C$\underline{H}$$_2$—CH$_2$—CH$_3$], 1.54 and 1.48 (3H, d, J=7.0 Hz, CH—C$\underline{H}$$_3$), 1.56-1.42 (2H, m, CH—CH$_2$-C$\underline{H}$$_2$—CH$_3$), 1.31 and 1.22 (3H, t, J=7.2 Hz, O—CH$_2$—C$\underline{H}$$_3$), 0.98 and 0.93 (3H, t, J=7.3 Hz, CH—CH$_2$—CH$_2$—C$\underline{H}$$_3$).

Preparation of Perindopril Eburmine

Example 5

Acylation of perhydroindole-2-carboxylic acid using N-[2-(ethoxycarbonyl)butyl]-N-ethoxycarbo-nylalanine To a solution of N-[2-(ethoxycarbonyl)butyl]-N-ethoxy-carbonylalanine (10.1 g, 35 mmol) in dichloromethane (35 mL) thionyl chloride (4.2 mL, 6.9 g, 58 mmol) was added in drops at 0-5° C. It was stirred at ambient temperature for 2-3 h. The solvent was evaporated to give a reddish oil. The residue was dissolved in THF (37.5 mL) and it was added to a suspension of perhydroindole-2-carboxylic acid (4.7 g, 28 mmol) in THF (37.5 mL). The suspension was refluxed with stirring for 4-4.5 h until a brownish solution was formed. After evaporation of the solvent the residue was dissolved in ethyl acetate (120 mL), t-butylamine (2.8 mL, 1.95 g, 27 mmol) in ethyl acetate (60 mL) was added slowly to the stirred solution resulting in separation of a crystalline mass. The mixture was heated until a solution was formed, then treated with charcoal. The crystalline product obtained after cooling was filtered to give perindopril eburmine (6.8 g, 55%).

Example 6

Acylation of perhydroindole-2-carboxylic acid using N-[2-(ethoxycarbonyl)butyl]-N-methoxycar-bonylalanine Perindopril eburmine was prepared analogously to Example 5, using N-[2-(ethoxycarbonyl)butyl]-N-methoxy-carbonylalanine (3.4 g, 12.5 mmol) and perhydroindole-2-carboxylic acid (1.7 g, 10 mmol). The crystalline product obtained was filtered to give perindopril eburmine (2.4 g, 54%).

Example 7

Acylation of perhydroindole-2-carboxylic Acid Using N-[2-(ethoxycarbonyl)butyl]-N-t-buthoxycar-bonylalanine Perindopril eburmine was prepared analogously to Example 5, using N-[2-5 (ethoxycarbonyl)butyl]-N-t-buthoxycarbonylalanine (0.69 g, 2.2 mmol) and perhydroin-dole-2-carboxylic acid (0.29 g, 1.7 mmol). The crystalline product obtained was filtered to give perindopril eburmine (0.37 g, 49%).

Example 8

Acylation of perhydroindole-2-carboxylic acid using N-[2-(ethoxycarbonyl)butyl]-N-benzyloxycar-bonylalanine Perindopril eburmine was prepared analogously to Example 5, using N-[2-(ethoxycarbonyl)butyl]-N-benzy-loxycarbonylalanine (1.41 g, 4 mmol) and perhydroindole-2-carboxylic acid (0.51 g, 3 mmol). The crystalline product obtained was filtered to give perindopril eburmine (0.60 g, 45%).

Example 9

Acylation of perhydroindole-2-carboxylic acid using N-[2-(ethoxycarbonyl)butyl]-N-ethoxycarbo-nylalanine To a solution of N-[2-(ethoxycarbonyl)butyl]-N-ethoxy-carbonylalanine (1.45 g, 5 mmol) in dichloromethane (7.5 mL) thionyl chloride (0.6 mL, 0.98 g, 8.5 mmol) was added dropwise at 0-5° C. It was stirred at ambient temperature for 2-3 h. The excess of thionyl chloride and the sulphur dioxide and hydrogen chloride formed was eliminated in slight vacuo. To the dichloromethane solution thus obtained was added perhydroindole-2-carboxylic acid (0.71 g, 4.2 mmol) and dichloromethane (5.0 mL). The suspension was refluxed with stirring for 2 h until a brownish solution was formed. After evaporation of the solvent the residue was dissolved in ethyl acetate (20 mL), whereupon t-butylamine (0.42 mL, 0.29 g, 4.05 mmol) in ethyl acetate (5.0 mL) was added slowly to the stirred solution resulting in separation of a crystalline mass. The mixture was heated until a solution was formed, then treated with charcoal. The crystalline product obtained after cooling was filtered to give perin-dopril eburmine (0.64 g, 35%).

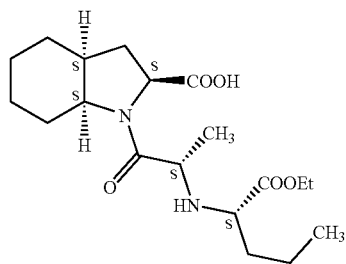
I
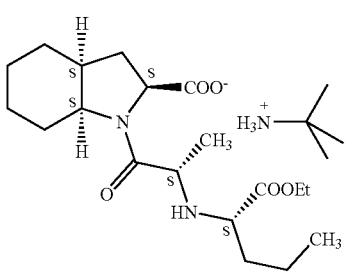
I'
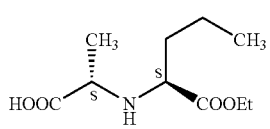
II
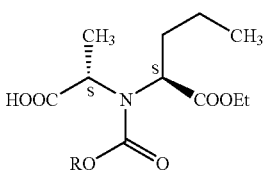
III
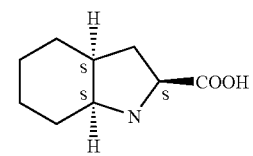
IV
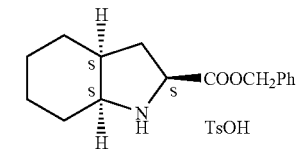
V
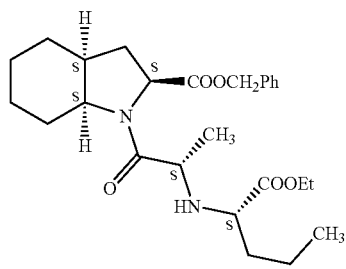
VI
-continued
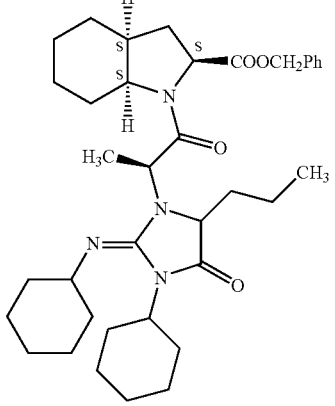
VII
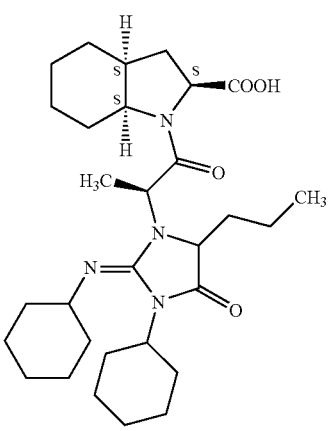
VII'
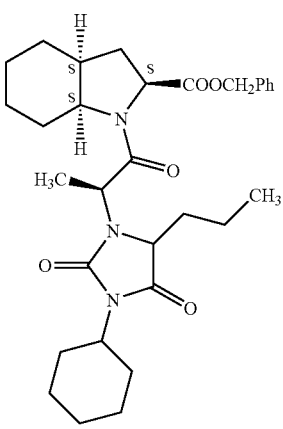
VIII -continued VIII'
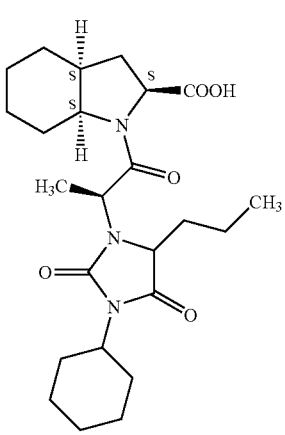

IX
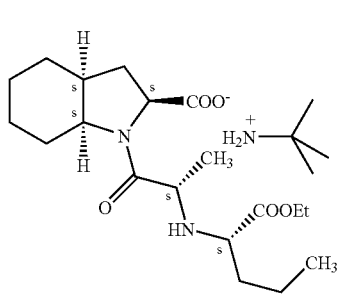

X

XI

XII

We claim:
1. A process for the preparation of 1-{2(S)-[1(S)-(ethoxycarbonyl)butylamino]propionyl}-(3aS,7aS)octahydroindol-2(S)-carboxylic acid of Formula I and the t-butylamine salt thereof of Formula I'

I
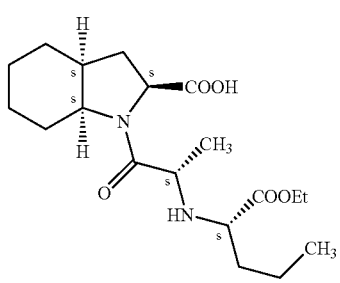

-continued

I'
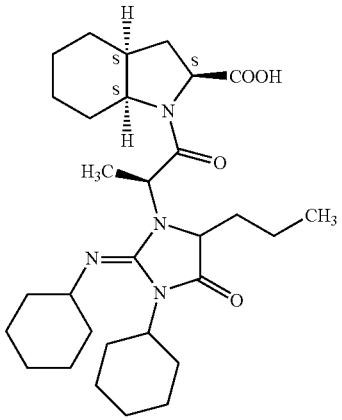

free of contaminations derivable from dicyclohexyl carbodiimide selected from the compounds of Formulas VII' and VIII':

VII'
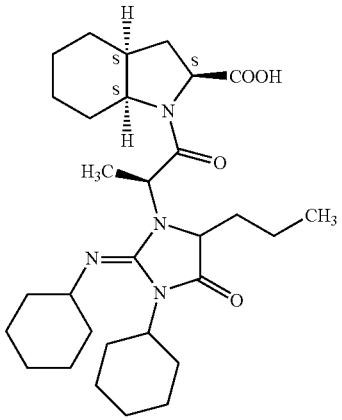

VIII'
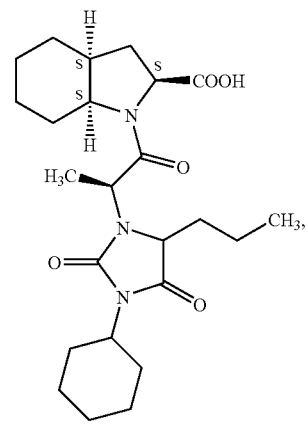

wherein
a compound of Formula II

II
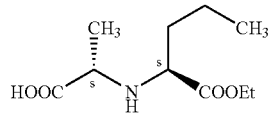

is acylated with a carbonic acid derivative selected from an alkyl chloroformate, benzyl chloroformate, and di-alkyl-dicarbonate to yield a compound of Formula III

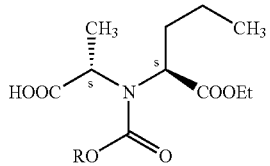

III wherein R represents lower alkyl or aryl-lower alkyl;

the compound of Formula III thus obtained is activated with thionyl chloride;

the activated intermediate thus obtained is reacted with a compound of Formula IV

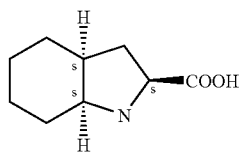

IV to provide the compound of Formula I, and, if desired, the compound of Formula I thus obtained is reacted with t-butylamine to provide the compound of Formula I'.

2. A process of claim 1, wherein the carbonic acid derivative is selected from methyl chloroformate, ethyl chloroformate, benzyl chloroformate and di-t-butyl dicarbonate.

3. A process of claim 1, wherein the acylation of the compound of Formula II is carried out in the presence of a base.

4. A process of claim 3, wherein the base is selected from an alkali carbonate, an alkali hydrogen carbonate and a tertiary amine.

5. A process of claim 4, wherein the base is selected from sodium carbonate, potassium carbonate and triethylamine.

6. A process of claim 1, wherein the acylation step is carried out in an inert organic solvent.

7. A process of claim 6, wherein the inert organic solvent is selected from a halogenated aliphatic hydrocarbon, an aromatic hydrocarbon, an ester or a ketone.

8. A process of claim 7, wherein the solvent is acetone.

9. A process of claim 1, wherein thionyl chloride is used in a molar ratio of 1.1-2 related to 1 mole of the compound of Formula III.

10. A process of claim 9, wherein thionyl chloride is used in a molar ratio of 1.5-1.7 related to 1 mole of the compound of Formula III.

11. A process of claim 1, wherein the activation of the compound Formula III with thionyl chloride is carried out in an inert organic solvent.

12. A process of claim 11, wherein the inert organic solvent is selected from a halogenated aliphatic hydrocarbon, an ester or an ether.

13. A process of claim 12, wherein the inert organic solvent is dichloromethane.

14. A process of claim 1, wherein the reaction of the activated intermediate with the compound of Formula IV is carried out in an inert organic solvent.

15. A process of claim 14, wherein the inert organic solvent is selected from a halogenated aliphatic hydrocarbon, an ester or an ether.

16. A process of claim 15, wherein the inert organic solvent is selected from tetrahydrofuran or dichloromethane.

* * * * *

UNITED STATES PATENT AND TRADEMARK OFFICE
CERTIFICATE OF CORRECTION

PATENT NO. : 7,326,794 B2
APPLICATION NO. : 10/503272
DATED : February 5, 2008
INVENTOR(S) : Gyula Simig et al.

It is certified that error appears in the above-identified patent and that said Letters Patent is hereby corrected as shown below:

On the Title Page, Item (75), Inventors: "Guyla Simig" should be -- Gyula Simig --.

On the Title Page, Item (30), Priority data: "02290206" should be -- 02290206.8 --.

Column 14, Line 22: "compound Formula III" should be -- compound of Formula III --.

Signed and Sealed this

Fifteenth Day of July, 2008

JON W. DUDAS
*Director of the United States Patent and Trademark Office*